United States Patent [19]

Gordon

[11] Patent Number: 5,704,577
[45] Date of Patent: Jan. 6, 1998

[54] WALKER-IV STAND COUPLER

[76] Inventor: Gray J. Gordon, 2110 Camel, Las Vegas, Nev. 89115

[21] Appl. No.: 540,990

[22] Filed: Oct. 11, 1995

[51] Int. Cl.$^6$ .......................................... A45B 3/00
[52] U.S. Cl. .................. 248/229.2; 135/66; 248/230.1; 403/385; 403/391
[58] Field of Search .................. 248/229.2, 229.25, 248/229.1, 229.15, 511, 512, 540, 541, 534, 230.1, 121; 135/65, 66, 67; 403/391, 389, 394, 396, 388, 385, 384, 354

[56] References Cited

U.S. PATENT DOCUMENTS

| | | | |
|---|---|---|---|
| 3,802,653 | 4/1974 | Nyulassie | 248/541 X |
| 4,234,094 | 11/1980 | Jorgensen | 403/391 X |
| 4,887,786 | 12/1989 | Stokes | 248/512 |
| 4,946,122 | 8/1990 | Ramsey et al. | 248/229.2 |
| 5,009,442 | 4/1991 | Schneider | 248/121 X |
| 5,177,927 | 1/1993 | Goya et al. | 403/389 X |
| 5,349,780 | 9/1994 | Dyke | 248/188.5 X |
| 5,358,205 | 10/1994 | Starkey et al. | 248/229.2 X |

FOREIGN PATENT DOCUMENTS

| | | | |
|---|---|---|---|
| 4004175 | 8/1991 | Germany | 248/511 |
| 544163 | 6/1958 | Italy | 248/229.25 |

*Primary Examiner*—Ramon O. Ramirez
*Assistant Examiner*—Derek J. Berger
*Attorney, Agent, or Firm*—Harry M. Weiss; Jeff Moy; Harry M. Weiss & Associates, P.C.

[57] ABSTRACT

A coupler made from cylindrical tubing has elastically deformable ends. Each end has a bifurcation. The bifrcations are mutually perpendicular. One of the bifurcations has a walker coupling location with an orthogonal projection that includes an arc of a circle that has a diameter substantially equal to the diameter of a cylindrical horizontal member of a walker. The other of the bifurcations has an IV stand coupler location with an orthogonal projection that includes an arc of a circle that has a diameter substantially equal to the diameter of a cylindrical member of an IV stand.

2 Claims, 2 Drawing Sheets

WALKER-IV STAND COUPLER

BACKGROUND OF THE INVENTION

1. Field of Invention

This invention relates generally to medical equipment and, more specifically, to coupling a walker to an IV stand.

2. Description of the Prior Art

When a person has been recently bedridden because of surgery or an illness, it is often desirable to have the person exercise to whatever extent possible. The exercise may take the form of ambulating by using what is known as a walker.

The walker is an aluminum frame with waist high left and right sides that have the general shape of an inverted U. Therefore, the walker has four legs. More particularly, each of the sides has a front leg and a rear leg.

In one type of walker, four wheels are respectively connected to the legs. In another type of walker, two wheels are respectively connected to the front legs.

The front leg and the rear leg of each side are contiguously connected by a connecting part that forms the horizontal portion of the inverted U shape. The front legs are connected together by horizontal members of the frame. The horizontal members are of a length that cause the sides to have a spacing therebetween where the person supports himself by grasping the left and right side connecting parts with his left and right hands, respectively.

The connecting parts each have a grip area covered with rubber or any other material suitable for providing a surface which the person may easily grasp. In order to ambulate, the person grasps the grip areas and urges the walker forward. Concurrently, most of the person's weight is supported through the person's hands and arms by the walker.

When the person receives fluids intravenously, a fluid pouch is usually connected to a portion of the person's body via a feed tube. The pouch is supported on an IV stand that is movable on castors. Because of the castors, care must be taken to prevent erratic movement of the IV stand that could cause a disconnection of the feed tube.

When the person simultaneously ambulates and receives the fluids intravenously, a hospital staff member stands side by side with the person and moves the IV stand to prevent the erratic movement. In a hospital corridor, for example, the person and the hospital staff member being side by side frequently impedes the passage of others through the corridor.

It should be understood that the use of the hospital staff member is expensive. Therefore, there is a need for a device that facilitates unassisted ambulation of the person while the person receives the fluids intravenously and does not impede the passage of others in the corridor.

SUMMARY OF THE INVENTION

An object of the present invention is to facilitate unassisted ambulation of a person that uses a walker while receiving fluids intravenously.

According to the present invention, a cylindrical coupling tube has elastically deformable ends that have a bifurcation. The bifurcations are mutually perpendicular. A first bifurcation extends from one end of the coupling tube to a walker coupling location of the tube. At the walker coupling location, the first bifurcation is of a size that makes it connectable to a horizontal member of a walker. A second bifurcation extends from the other end of the tube to an IV stand coupling location of the tube. At the IV stand coupling

2 location, the other bifurcation is of a size that makes it connectable to an IV stand.

The invention provides an inexpensive apparatus that permits unassisted ambulation of a person that uses a walker while receiving fluids intravenously.

Other objects, features, and advantages of the invention should be apparent from the following description of the preferred embodiment as illustrated in the accompanying drawing.

DESCRIPTION OF THE PREFERRED EMBODIMENT

Figure 1:
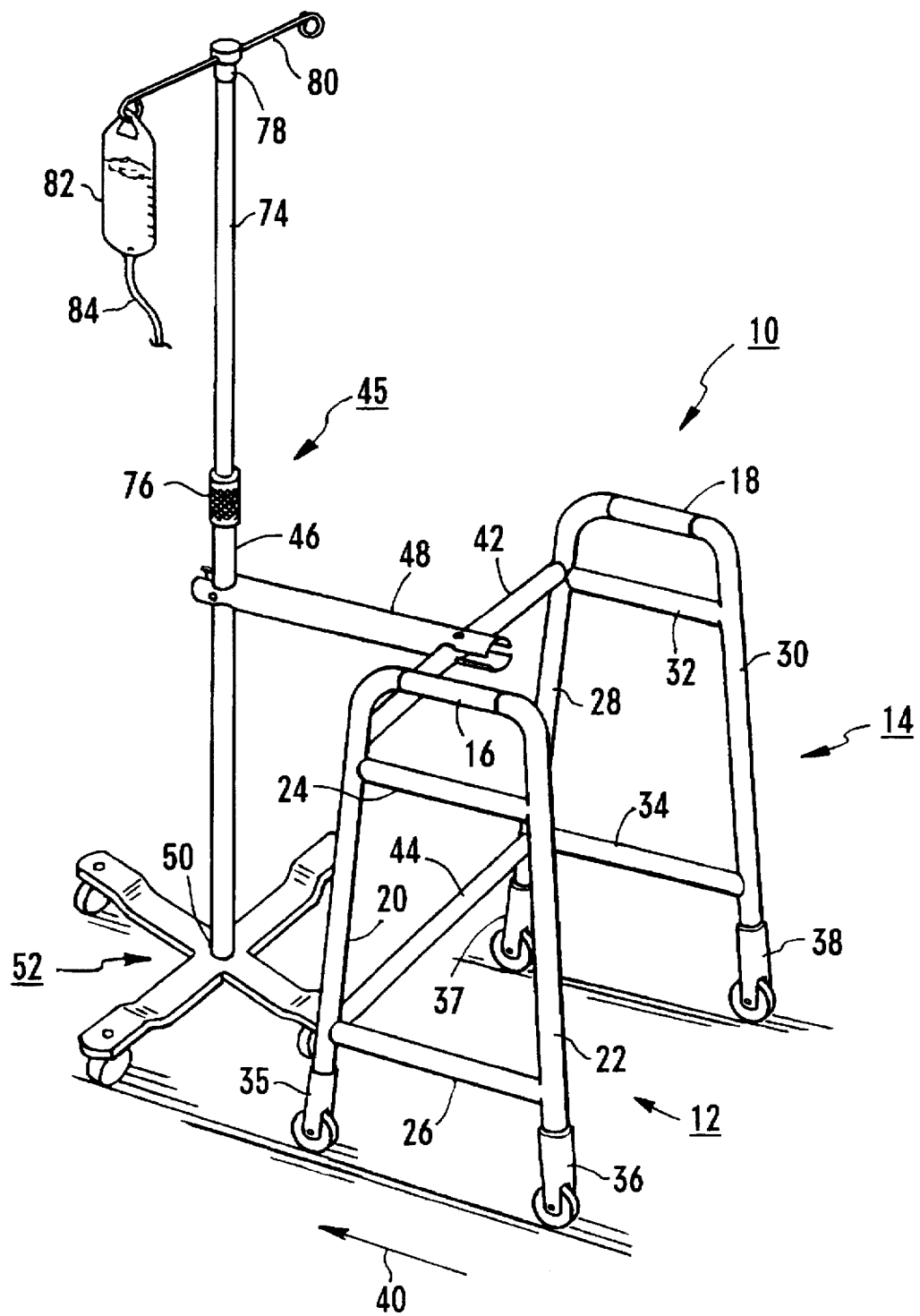
FIG. 1 is a perspective view of the preferred embodiment of the present invention.

As shown in FIG. 1, a walker 10 includes similar sides 12, 14 that are formed from aluminum tubing to have the general shape of an inverted U. The sides 12, 14 have grips 16, 18, respectively, where there is a rubber covering. The grips 16, 18 are approximately waist high to a person that uses the walker 10.

The side 12 has a front leg 20 and a rear leg 22 that are connected together by braces 24, 26 for structural rigidity. Similarly, the side 14 has a front leg 28 and a rear leg 30 that are connected together by braces 32, 34 for structural rigidity.

In this embodiment, the legs 20, 22, 28, 30 are connected to wheel assemblies 35, 36, 37, 38, respectively. It should be understood that the wheel assemblies 35–38 are of a type that provide non-skid rolling of the walker 10 in the direction of an arrow 40 and in an opposite direction therefrom. In an alternative embodiment, the wheel assemblies 36, 38 are not included.

An upper portion of the legs 20, 28 are connected together by a cylindrical horizontal member 42 of the walker 10 that is made from aluminum tubing. A lower portion of the legs 20, 28 are connected together by a horizontal member 44 that is similar to the member 42. The members 42, 44 are of a length that cause the sides 12, 14 to have a spacing therebetween where the person supports himself by grasping the grips 16, 18 with his left and right hands, respectively. Walker 10 is of a type well known to those skilled in the art.

As explained hereinafter, the member 42 is used to couple the walker 10 to an IV stand. Because of the coupling, whenever the walker 10 moves, the IV stand correspondingly moves, thereby eliminating the need for a hospital staff member to move the IV stand.

The member 42 is fixedly connected to an IV stand 45 at an outer vertical cylindrical member 46 thereof through a coupler 48 which is more fully described hereinafter. The IV stand 45 is of a type that is well known to those skilled in the art.

An end 50 of the outer member 46 is connected to a castor assembly 52. Therefore, because of the coupler 48 and the castor assembly 52, when the person causes movement of the walker 10, the IV stand 45 correspondingly moves.

Figure 2:
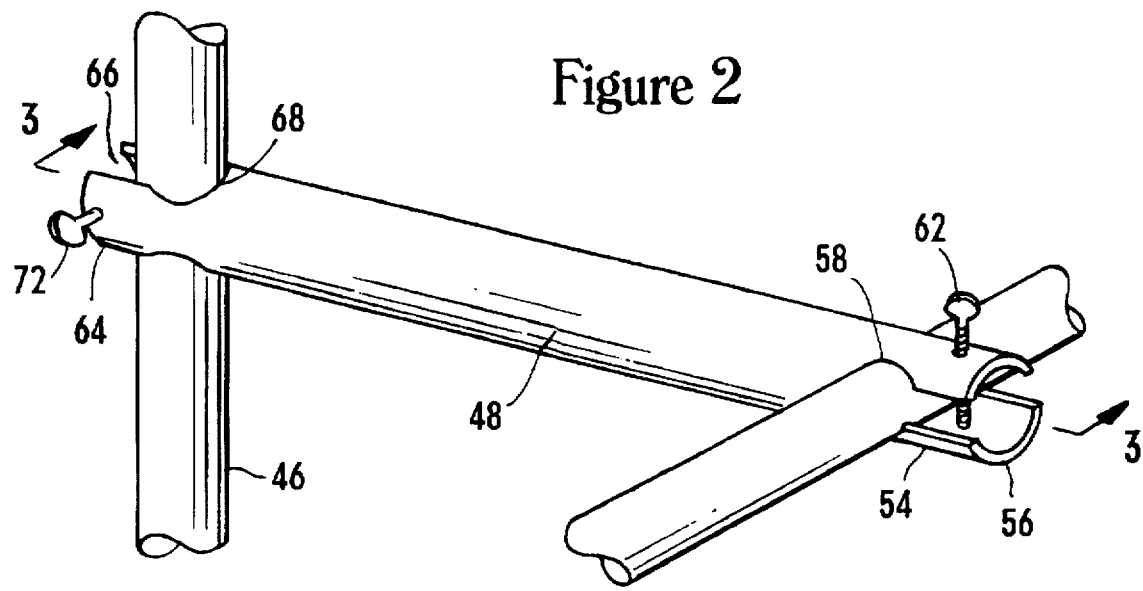
FIG. 2 is an enlarged view of a portion of FIG. 1.

As shown in FIG. 2, the coupler 48 is a cylindrical tube with an elastically deformable walker coupling end 54 that is bifurcated. Preferably, the coupler 48 is made from poly vinyl chloride.

An entrance region 56 of the walker end bifurcation is formed by diametrically opposite slots that are parallel to the central axis of the coupler 48 (not shown) through the wall thereof. The walker end bifurcation extends to a walker coupling location 58.

Figure 3:
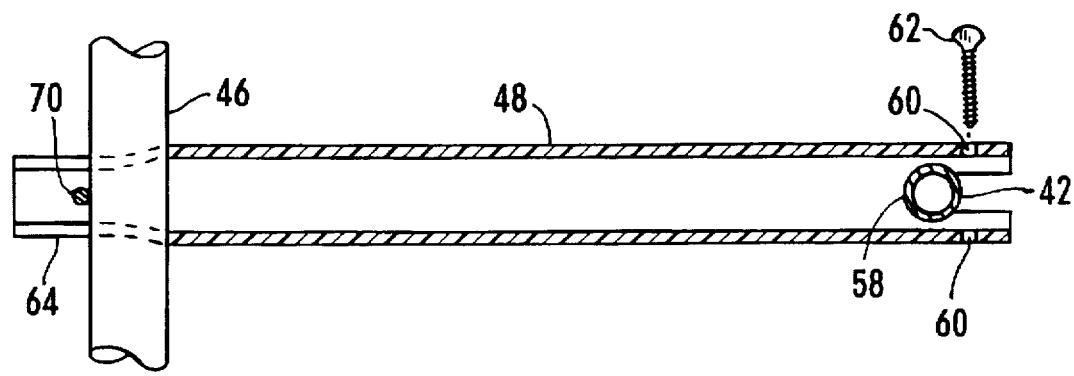
FIG. 3 is a section of FIG. 2 taken along the line 3—3.

As shown in FIG. 3, the location 58 has a planar projection that includes an arc of a circle having a diameter substantially equal to the diameter of the member 42. Because the arc of the circle and the member 42 have diameters that are substantially equal, the coupler 48 is connected to the member 42 by elastically deforming the region 56 to fit the member 42 into the coupling location 58. The entrance region 56 has a pair of threaded holes 60 that are located diametrically opposite from each other. When the member 42 is within the location 58, a thumbscrew 62 is screwed into the holes 60 thereby maintaining the member 42 within the walker end bifurcation.

The coupler 48 additionally has an IV stand coupler end 64 with a bifurcation similar to the walker end bifurcation described hereinbefore. However, the bifurcations at the ends 54, 64 are mutually perpendicular.

The IV stand end bifurcation has an entrance region 66 (FIG. 2) and an IV stand coupling location 68 that are similar to the region 56 and the location 58, respectively. Moreover, the location 68 has a relationship to the member 46 that is similar to the relationship of the location 58 to the member 42. Because the bifurcations at the ends 54, 64 are mutually perpendicular, the slots of the walker end bifurcation in the region 56 are rotated ninety degrees about the central axis of the coupler 48 from corresponding slots of the IV stand end bifurcation in the region 66.

The entrance region 66 has a pair of threaded holes 70 that are similar to the holes 60. When the member 46 is within the location 68, a thumbscrew 72, similar to the thumbscrew 62, is screwed into the holes 70 thereby maintaining the member 46 within the location 68.

The IV stand 45 (FIG. 1) additionally includes an inner vertical cylindrical member 74 that telescopically extends from the member 46. A desired extension of the member 74 is maintained by a manually operated clamp 76.

The top 78 of the member 74 is connected to a crossbar support 80 from which an IV pouch 82 is suspended. The pouch 82 is connected to the person through a tube 84.

While the invention has been particularly shown and described with reference to a preferred embodiment thereof, it will be understood by those skilled in the art that changes in form and detail may be made therein without departing from the spirit and scope of the invention.

I claim:

1. An apparatus for facilitating unassisted ambulation of a person using a walker and needing to receive fluids intravenously comprising, in combination:

a walker having a cylindrical horizontal member;

an IV stand spaced from said walker and having a cylindrical vertical member; and a hollow cylindrical tube having one end connected to said cylindrical horizontal member of said walker and another end connected to said cylindrical vertical member of said IV stand, said one end of said hollow cylindrical tube having first quick attach-quick detach snap on means for rapidly connecting to by snapping on and for rapidly disconnecting from by snapping off said cylindrical horizontal member of said walker, said first quick attach-quick detach snap on means comprising a first pair of flexible, spaced-apart arcuate shaped members provided with a transverse cylindrical shaped opening having a diameter substantially equal to a diameter of said cylindrical horizontal member of said walker, said cylindrical horizontal member of said walker being located in said transverse cylindrical shaped opening in said first pair of flexible, spaced-apart arcuate shaped members, each one of said first pair of flexible, spaced-apart arcuate shaped members having an opening therethrough at an end portion thereof, removable fastening device means penetrating through said opening of each one of said first pair of flexible, spaced-apart arcuate shaped members for securely locking in place in said transverse cylindrical shaped opening said cylindrical horizontal member of said walker, said other end of said cylindrical tube having second quick attach-quick detach snap on means for rapidly connecting to by snapping on and for rapidly disconnecting from by snapping off said cylindrical vertical member of said IV stand, said second quick attach-quick detach snap on means comprising a second pair of flexible, spaced-apart arcuate shaped members provided with a transverse cylindrical shaped opening having a diameter substantially equal to a diameter of said cylindrical vertical member of said IV stand, said cylindrical vertical member of said IV stand being located in said transverse cylindrical shaped opening in said second pair of flexible, spaced-apart arcuate shaped members, each one of said second pair of flexible, spaced-apart arcuate shaped members having an opening therethrough at an end portion thereof, removable fastening device means penetrating through said opening of each one of said second pair of flexible, spaced-apart arcuate shaped members for securely locking in place in said transverse cylindrical shaped opening said cylindrical vertical member of said IV stand, said transverse cylindrical shaped opening in said first pair of flexible, spaced-apart arcuate shaped members being orthogonal to said transverse cylindrical shaped opening in said second pair of flexible, spaced-apart arcuate shaped members.

2. The apparatus of claim 1 wherein said cylindrical tube is a light weight PVC tube, each one of said removable fastening device means of said first and said second pair of flexible, spaced-apart arcuate shaped members being a thumbscrew.

* * * * *